(12) United States Patent
Andersson et al.

(10) Patent No.: US 6,210,897 B1
(45) Date of Patent: Apr. 3, 2001

(54) IDENTIFICATION OF CANINE LEUKOCYTE ADHESION DEFICIENCY IN DOGS

(76) Inventors: Leif Andersson, Bergagatan 30, S-752 39 Uppsala (SE); James Kijas, Borjegatan 54B, 752 29 Uppsala (SE); Sophie Gafvert, St. Bjorklunda 1470, S-150 23 Enhorna (SE); Gunilla Wigh-Trowaldh, Ralsvagen 9D, S-756 33 Uppsala (SE); Ake Hedhammar, Genvagen 13, S-182 34 Dandery (SE)

( * ) Notice: Subject to any disclaimer, the term of this patent is extended or adjusted under 35 U.S.C. 154(b) by 0 days.

(21) Appl. No.: 09/393,554

(22) Filed: Sep. 10, 1999

Related U.S. Application Data

(60) Provisional application No. 60/136,099, filed on May 26, 1999.

(51) Int. Cl.[7] .............................. C12Q 1/68; C12P 19/34; C07H 21/04
(52) U.S. Cl. ........................ 435/6; 435/91.1; 435/91.2; 536/23.3; 536/24.3; 536/24.33
(58) Field of Search ............................ 435/6, 91.1, 91.2, 435/183; 536/23.1, 23.3, 24.3, 24.33, 25.3

(56) References Cited

U.S. PATENT DOCUMENTS

| | | |
|---|---|---|
| 5,395,929 | 3/1995 | Corbi et al. . |
| 5,514,555 | 5/1996 | Springer et al. . |
| 5,602,307 | 2/1997 | Beaudet et al. . |
| 5,686,265 | 11/1997 | Corbi et al. . |
| 5,770,686 | 6/1998 | Gallatin et al. . |
| 5,773,218 | 6/1998 | Gallatin et al. . |
| 5,811,517 | 9/1998 | Gallatin et al. . |
| 5,837,822 | 11/1998 | Gallatin et al. . |
| 5,849,896 | 12/1998 | Springer et al. . |
| 5,869,262 | 2/1999 | Gallatin et al. . |
| 5,880,268 | 3/1999 | Gallatin et al. . |
| 5,989,843 | 11/1999 | Gallatin et al. . |

OTHER PUBLICATIONS

Genbank Registry No. 248563–06–6, Nov. 1999.*
Promega 1993/94 Catalog, p. 90, Nov. 1999.*
Landegren et al., "Reading Bits of Genetic Information: Methods for Single–Nucleotide Polymorphism Analysis," *Genome Res.* 8:769–776 (1998).
Connolly, "Canine Granulocytopathy Syndrome in Irish Setters," *Journal of Small Animal Practice* 38:591 (Dec. 1997).
Trowald–Wigh et al., "Canine Neutrophil Adhesion Proteins and Fc–Receptors in Healthy Dogs and Dogs with Adhesion Protein Deficiency, as Studied by Flow Cytometry," *Veterinary Immunology and Immunopathology* 38:297–310 (1993).
Gerardi, "Bovine Leukocyte Adhesion Deficiency: A Brief Overview of a Modern Disease and Its Implications," *Acta Veterinaria Hungarica* 44:1–8 (1996).
Gerardi, "Bovine Leucocyte Adhesion Deficiency: a Review of a Modern Disease and Its Implications," *Veterinary Science* 61:183–186 (1996).
Cox et al., "Leucocyte Adhesion Deficiency in Cattle and Dogs: a Genetic Defect of the Immune System," *Vlaams Diergeneeskd Tijdschr* 62:71–79 (1993) (abstract).
Renshaw et al., "Canine Granulocytopathy Syndrome: Neutrophil Dysfunction in a Dog with Recurrent Infections," *Journal of the American Veterinary Medical Association* 166:443–477 (1975).
Renshaw et al., "Canine Granulocytopathy Syndrome: An Inherited Disorder of Leukocyte Function," *A. J. Pathol.* 95:731–744 (1979).
Giger et al., "Deficiency of Leukocyte Surface Glycoproteins Mo1, LFA–1, and Leu M5 in a Dog With Recurrent Bacterial Infections: An Animal Model," *Blood* 69:1622–1630 (1987).
Trowald–Wigh et al., "Leucocyte Adhesion Protein Deficiency in Irish Setter Dogs," *Vet. Immun. & Immunopath.* 32:261–280 (1992).

* cited by examiner

Primary Examiner—Bradley L. Sisson
(74) Attorney, Agent, or Firm—Nixon Peabody LLP

(57) ABSTRACT

The present invention relates to an isolated nucleic acid molecule encoding canine leukocyte integrin β-2 subunit having a Cys36Ser missense mutation, wherein the missense mutation is indicative of a carrier of canine leukocyte adhesion deficiency. The present invention also relates to a method for identifying dogs which are carriers of or are affected with canine leukocyte adhesion deficiency. This method includes obtaining a biological sample from a dog and testing the biological sample for a Cys36Ser missense mutation in a gene encoding leukocyte integrin β-2 subunit, wherein the missense mutation in one allele is indicative of a carrier of canine leukocyte adhesion deficiency and the missense mutation in both alleles is indicative of a dog affected with canine leukocyte adhesion deficiency.

16 Claims, 3 Drawing Sheets

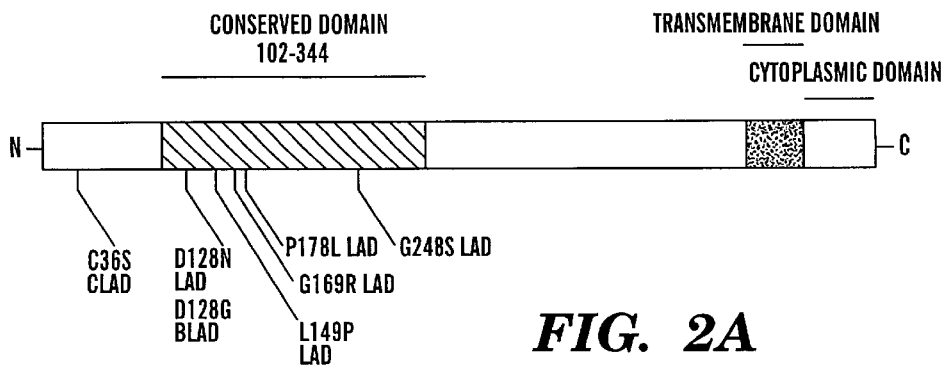

FIG. 2A

```
                                                                    60
Dog     MLRHSSLLLTLEGLLFLWAASCQECTKYKVSTCRDCVESGPGCAWCQKLNFTGLGEPDSV
Cattle  ...QRPQ..L.A...A.QSVLS....N.........I................Q.....I
Human   ..GLRPP..A.V...S.GCVLS.....F...S..E.I......T.........P.D...I
Pig     ..CRC.P..L.V...T.RS.LS...A.........I.................S.Q.....
Mouse   ..GPH....A.A..F..GS.VS.........S....IQ.....S.........P.....L 120
Dog     RCDTREQLLLKGCAADDIMDPQSLAEIQEDKKGGRQQLSPQKVTLYLRPGQAAAFNVTFR
Cattle  .....AE..S...P.....E.K....TRDSQA.S.K.....E...........V.......
Human   .....P...MR.........T....T...HN..QK..........................
Pig     .........A...V....V..R....T..QA..QK.....................T......
Mouse   .....A........P.......R.I.NPEF.QR.Q.K........................

240
Dog     RAKGYPIDLYYLMDLSYSMLDDLINVKKLGGDLLRALNEITESGRIGFGSFVDKTVLPFV
Cattle  ..............V...V..............G...........................
Human   ..................R...........................................
Pig     ...............................................................
Mouse   ..................N.........Q..................................

300
Dog     NTHPEKLKNPCPNKEKECQAPFAFRHVLKLTNNSNKFQTEVGKQLISGNLDAPEGGLDAM
Cattle  .......R..........P............D..KQ.E........................
Human   ....D..R..........P.............Q..............................
Pig     .......R........................D...Q..........................
Mouse   .......R.......A..P.............D...Q..........................

360
Dog     MQVAACPEQIGWRNVTRLLVFATDDGFHFAGDGKLGAILTPNDGRCHLEDNMYKRSNEFD
Cattle  ........E................................................L..S.....
Human   ........E................................................L........
Pig     ........E................................................L..S.....
Mouse   ........E..........................................................

344
Dog     YPSVGQLAHKLAESNIQPIFAVTKRMVTTYEKLTEVIPKSAVGE
Cattle  .........................K..K.......I........
Human   ............N.........S...K.......I........
Pig     .....................K..K......DI........
Mouse   ..........S.............K..K.......I........
```

FIG. 2B

```
          31   32   33   34   35   36   37   38   39
Normal    AGC  ACG  TGC  CGG  GAC  TGT  GTG  GAG  TCG
Affected  ...  ...  ...  ...  ...  .C.  ...  ...  ...

Normal    Ser  Thr  Cys  Arg  Asp  Cys  Val  Glu  Ser
Affected  ...  ...  ...  ...  ...  Ser  ...  ...  ...
```

IDENTIFICATION OF CANINE LEUKOCYTE ADHESION DEFICIENCY IN DOGS

This application claims the benefit of U.S. Provisional Patent Application No. 60/136,099, filed May 26, 1999, which is hereby incorporated by reference.

FIELD OF THE INVENTION

The present invention relates to the identification of a missense mutation in the gene encoding the leukocyte β-2 integrin subunit in dogs, particularly Irish Setters, and a method for identifying dogs that are carriers of or are affected with canine leukocyte adhesion by detecting the presence of the missense mutation.

BACKGROUND OF THE INVENTION

Leukocyte adhesion deficiency (LAD) in humans is an autosomal recessive disorder characterized by severe recurrent infections, delayed umbilical cord separation, impaired wound healing, severe gingivitis, persistent leucocytosis, and absent pus formation (Anderson et al., "The Severe and Moderate Phenotypes of Heritable Mac-1, LFA-1 Deficiency: Their Quantitative Definition and Relation to Leukocyte Dysfunction and Clinical Features," *J. Infect. Dis.*, 152:668–689 (1985); Guneser et al., "An Infant With Severe Leucocyte Adhesion Deficiency," *Acta Pediatr.*, 85:622–624 (1996)). The clinical manifestations of LAD are caused by diminished or absent expression of the β-2 integrin (CD18) molecule (Arnaout et al., "Deficiency of a Leukocyte Surface Glycoprotein (LFAI) in Two Patients With Mol Deficiency." *J. Clin. Invest.*, 74: 1291–1300 (1984), El Habbal et al., "Leucocyte Adhesion Deficiency," *Archives of Disease in Childhood*, 69:463–466 (1993)). Integrins are heterodimeric glycoproteins composed of an α and β subunit and are known to play a central role in cell-cell adhesion events. The four leukocyte integrin α subunits αL (CD11a), αM (CD11b), αX (CD11c), and αD (CD11d) each associate with the common β-2 subunit (CD18) to form the antigens LFA-1, Mac-1, p150,95, and $\alpha_D\beta_2$, respectively (Springer et al., "Inherited Deficiency of the Mac-1, LFA-1, p150,95 Glycoprotein Family and Its Molecular Basis," *J. Exp. Med.*, 160:1901–1918 (1984); Danilenko et al., "A Novel Canine Leukointegrin, Alpha d Beta 2, Is Expressed by Specific Macrophage Subpopulations in Tissue and a Minor CD8+Lymphocyte Subpopulation in Peripheral blood, *J. Immunol.*, 155:35–44 (1995)). Defects in the common β2 subunit prevent surface expression of all four heterodimers, and result in the LAD phenotype.

The human β-2 integrin gene (ITGB2) is composed of 16 exons spanning approximately 40 kb of genomic sequence (Weitzman et al., "The Gene Organization of the Human Integrin p2 Subunit (CD18)," FEBS, 294:97–103 (1991)). Mutation screening of ITGB2 has revealed a spectrum of mutations in human LAD patients, the majority of which are missense mutations changing residues in a highly conserved region of the extracellular domain (Arnaout et al., "Point Mutations Impairing Cell Surface Expression of the Common Beta Subunit (CD 18) in a Patient with Leukocyte Adhesion Molecule (Leu-CAM) Deficiency." *J. Clin. Invest.*, 85:977–981 (1990); Wardlaw et al., "Distinct Mutations in Two Patients with Leukocyte Adhesion Deficiency and Their Functional Correlates," *J. Esp. Med.*, 172:335–345 (1990); Matsuura et al., "Leukocyte Adhesion Deficiency: Identification of Novel Mutations in Two Japanese Patients with a Severe Form," *Biochem. Biophys. Res. Commun.*, 184:1460–1467 (1992)). In addition, a mutation at the initiation codon (Sligh et al., "An Initiation Codon Mutation in CD18 in Association with the Moderate Phenotype of Leukocyte Adhesion Deficiency," *J. Biol. Chem.*, 267:714–718 (1992)), frameshift mutations (Back et al., "Identification of Two Molecular Defects in a Child with Leukocyte Adherence Deficiency," *J. Biol. Chem.*, 267:5482–5487 (1992)), and splice mutations (Nelson et al., "Genetic Cause of Leukocyte Adhesion Molecule Deficiency: Abnormal Splicing and a Missense Mutation in a Conserved Region of CD18 Impair Cell Surface Expression of Beta-2 Integrins," *J. Biol. Chem.*, 267:3351–3357 (1992)) have been shown to result in LAD. On the basis of very similar clinical symptoms, leukocyte β2 integrin expression was examined and found to be defective in American Holstein-Friesian cattle with a severe immunodeficiency syndrome (Kehrli et al., "Molecular Definition of the Bovine Granulocytopathy Syndrome: Identification of Deficiency of the Mac-1 (CD11b/CD 18) Glycoprotein." *Am. J. Vet. Res.*, 51:1826–1836 (1990)). Sequence analysis of bovine ITGB2 revealed that all affected calves tested were homozygous for a missense mutation (D128G). Thus, the bovine form of the disease (BLAD) is genetically equivalent to that of human LAD (Shuster et al., "Identification and Prevalence of a Genetic Defect that Causes Leukocyte Adhesion Deficiency in Holstein Cattle," *Proc. Natl. Acad. Sci. USA*, 89:9225–9229 (1992))

Renshaw et al., "Canine Granulocytopathy Syndrome: Neutrophil Dysfunction in a Dog with Recurrent Infections," *J. Am. Vet. Med. Assoc.*, 166:443–447 (1975) described a case of granulocytopathy with impaired leukocyte bactericidal activity and life-threatening infections in an Irish Setter. Subsequent breeding experiments demonstrated an autosomal recessive nature of the defect (Renshaw et al., "Canine Granulocytopathy Syndrome: An Inherited Disorder of Leukocyte Function," *Am. J. Pathol.*, 95,731 –743 (1979)). Deficient expression of the CD11/CD18 molecule was subsequently identified in an animal with recurrent infections (Giger et al., "Deficiency of Leukocyte Surface Glycoproteins Mol, LFA-1, and Leu M5 in a Dog with Recurrent Bacterial Infections: An Animal Model," *Blood*, 69:1622–1630 (1987)). Further, defective adhesion and C3b medicated phagocytosis were demonstrated in 12 Irish Setter puppies with severe infections of omphalophlebitis, skin infections, osteomyelitis, and gingivitis (Trowald-Wigh et al., "Leucocyte Adhesion Protein Deficiency in Irish Setter Dogs," *Veterinary Immunology and Immunopathology*, 32:261–380 (1992)), providing a final confirmation of the existence of canine leukocyte adhesion deficiency (CLAD). CLAD is a fatal immunodeficiency disease so far only found in Irish Setters. To date, the molecular defect responsible for CLAD is unknown, making molecular identification of carrier animals impossible.

The present invention is directed to overcoming the above-noted deficiencies in the prior art.

SUMMARY OF THE INVENTION

The present invention relates to an isolated nucleic acid molecule encoding canine leukocyte integrin β-2 subunit having a Cys36Ser missense mutation, wherein the missense mutation is indicative of a carrier of canine leukocyte adhesion deficiency.

The present invention also relates to a method for identifying dogs which are carriers of or are affected with canine leukocyte adhesion deficiency. This method includes obtaining a biological sample from a dog and testing the biological sample for a Cys36Ser missense mutation in a gene encoding leukocyte integrin β-2 subunit, wherein the missense mutation in one allele is indicative of a carrier of canine leukocyte adhesion deficiency and the missense mutation in both alleles is indicative of a dog affected with canine lelikocyte adhesion deficiency.

The present invention has enabled a DNA-based diagnostic test for CLAD to be developed, and, therefore, a technique for identifying animals for breeding In particular, identifying carriers of CLAD through identification of the Cys36Ser missense mutation in the gene encoding canine leukocyte integrin β-2 subunit allows a breeder to eliminate the carriers from breeding stock.

BRIEF DESCRIPTION OF THE DRAWINGS

FIGS. 2A and 2B show the features of the ITGB2 gene. FIG. 2A shows the relative position of the transmembrane and cytoplasmic domains. Previously identified gene lesions in both man and cattle are shown to occur within the highly conserved region (Huang et al., "Folding of the Conserved Domain but not of Flanking Regions in the Integrin β2 Subunit Requires Association with the α Subunit," *Proc. Natl. Acad. Sci. USA*, 94:3156–3161 (1997), which is hereby incorporated by reference; striped box). FIG. 2B shows the alignment of ITGB2 amino acid positions 1 to 344 in dog (SEQ. ID. No. 1), cattle (SEQ. ID. No. 2), human (SEQ. ID. No. 3), pig (SEQ. ID. No. 4), and mouse (SEQ. ID. No. 5). Positions with sequence identity to the dog are indicated with a dot and the position of the canine leukocyte adhesion deficiency (CLAD) mutation C36S is denoted with a vertical arrow.

FIG. 3A shows the nucleotide (SEQ. ID. No. 6; SEQ. ID. No. 7) and corresponding amino acid sequence (SEQ. ID. No. 8; SEQ. ID. No. 9) for codon 31–38 of ITBG2 from a normal and an affected dog. FIG. 3B shows a diagnostic DNA test in the form of a gel-based Oligonucleotide Ligation Assay (OLA) showing the three different genotypes, homozygous normal (G/G), carrier (G/C), and affected (C/C). Hex and Rox refer to the two fluorescent dyes used for detection of PCR and OLA products.

DETAILED DESCRIPTION OF THE INVENTION

Figures 1A, 1B, 1C:
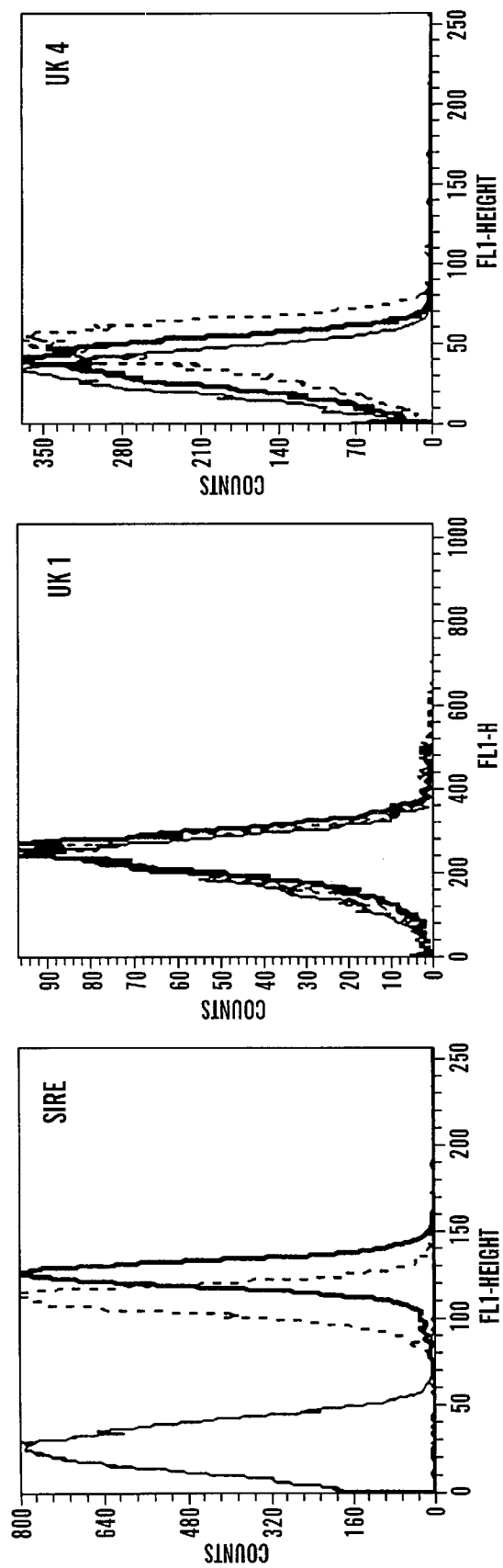
FIGS. 1A–C show the FACS analysis of one heterozygous parent (Sire) (FIG. 1A), one affected puppy with total lack of expression (UK1) (FIG. 1B), and one affected puppy with partial expression (UK4) (FIG. 1C). Staining was carried out with control antibody (thin line), CD11b/ITGA2 (dashed line) and CD18/ITGB2 (thick line).

The present invention relates to an isolated nucleic acid molecule encoding canine leukocyte integrin β-2 subunit having a Cys36Ser missense mutation, wherein the missense mutation is indicative of a carrier of canine leukocyte adhesion deficiency.

The DNA and amino acid sequences for the leukocyte integrin β-2 subunit (CD 18) in Irish Setters have previously been identified. The wildtype gene sequence for ITGB2, which encodes the leukocyte integrin β-2 subunit, is provided in SEQ. ID. No. 10 as follows:

```
GAATTCCCAC CGAGGTCACC GGCATCAGCG GGGACATGCT GCGCCACAGC TCCCTGCTGC

TCACCCTGGA GGGTCTGCTC TTTCTCTGGG CCGCGTCCTG CCAGGAGTGC ACCAAGTACA

AAGTGAGCAC GTGCCGGGAC TGTGTGGAGT CGGGGCCCGG CTGCGCCTGG TGCCAGAAGC

TGAACTTCAC TGGGCTAGGG GAGCCCGACT CCGTTCGCTG TGACACCCGA GAGCAGCTGC

TGCTGAAAGG ATGTGCGGCT GACGACATCA TGGACCCTCA GAGCCTGGCC GAGATCCAGG

AGGACAAGAA GGGCGGCCGG CAGCAGCTGT CCCCGCAGAA AGTGACGCTC TACCTGAGAC

CAGGTCAGGC GGCTGCCTTC AATGTGACCT TCCGGCGGGC CAAGGGCTAC CCCATCGACC

TGTACTACCT GATGGATCTG TCCTACTCCA TGCTGGACGA CCTCATCAAC GTCAAGAAGC

TGGGGGGCGA CCTGCTGCGG GCGCTCAACG AAATCACCGA GTCCGGCCGC ATCGGCTTCG

GGTCTTTCGT GGACAAGACG GTGCTCCCCT TCGTCAACAC GCACCCCGAG AAGCTGAAGA

ACCCGTGCCC CAACAAGGAG AAGGAGTGCC AGGCGCCGTT CGCCTTCAGA CACGTGCTGA

AGCTCACGAA CAACTCCAAC AAGTTCCAGA CGGAGGTCGG GAAGCAGCTG ATCTCGGGGA

ACCTGGACGC GCCCGAGGGC GGGCTGGATG CCATGATGCA GGTCGCCGCG TGCCCGGAGC

AAATCGGCTG GCGCAACGTC ACTCGGCTGC TGGTGTTCGC CACGGACGAC GGCTTCCACT

TTGCGGGCGA CGGGAAGCTG GGTGCCATCC TGACCCCCAA TGACGGCCGC TGCCACCTGG

AGGACAACAT GTACAAGAGG AGCAATGAAT TTGACTACCC GTCGGTGGGC CAGCTGGCAC

ACAAACTGGC CGAAAGCAAC ATCCAGCCCA TCTTCGCGGT GACCAAGAGA ATGGTGACGA

CCTATGAGAA GCTCACCGAG GTCATCCCCA AGTCAGCGGT CGGGGAGCTG TCGGACGATT

CCAGCAACGT GGTCCAGCTC ATCAAGAACG CCTACAACAA ACTGTCCTCC AGGGTCTTCC

TGGACCACAG CCTGGCCCCC AGCACCCTCA AGGTCACCTA TGACTCCTTC TGCAGTAACG
```

-continued

```
GGGTGTCGCA GGTGGACCAG CCCAGAGGGG ACTGCGACGG CGTCCAGATC AACGTCCCGA

TCACCTTCCA GGTGAAGGTC ACGGCCACGG AGTGCATCCA GGAGCAGTCG TTTATAATCC

GGGCACTGGG CTTCACGGAC ACAGTGACCG TGCACGTCAT CCCCCAGTGC GAGTGCCAGT

GCCGGGACGT GGGCCAGGAC CACGGCCTCT GCAGCGGCAA GGGCTCCCTG GAGTGTGGCA

TCTGCAGGTG TGAGGCTGGC TACATCGGGA AGAACTGCGA GTGCCTGACG CACGGCCGCA

GCAGCCAGGA GCTGGAGGGC AGCTGTCGGA GGGACAACAG CTCTCTCATC TGCTCGGGGC

TGGGGGACTG CCTCTGCGGG CAGTGCGTGT GCCACAGGAG CGACGTTCCC AACAAGAACA

TCTTCGGGCG CTACTGCGAG TGTGACAATG TCAACTGCGA GCGCTATGAC GGGCAGGTGT

GCGGGGGTAA AGTTCGGGGC TCCTGCAACT GCGGCAAGTG CCAGTGTGAG CAGAACTACG

AGGGCTCGGC GTGCCAGTGC GTGAAGTCCA CCCAGGGCTG CCTGAGCACG GAGGGCATCG

AGTGCAACGG GCGCGGCCGC TGTCGCTGTA ACGTGTGCGA GTGCGACGGG GGCTACCAGC

CGCCGCTGTG CGGGGACTGC CTGGGCTGCC CGTCGCCCTG TGGCCGGTAC ATCACCTGTG

CCCAGTGCCT GAAGTTCAAG CAGGGCCCCT CGGGGAGGAA CTGCAGCGTG GAGTGTGGGA

ACGTGGGCCT GCTGAGCAAA CCCCCAGAGA AGGGGCGCAG GTGCAAGGAG CGGGATCTGG

AGGGCTGCTG GATCACCTAC ACGCTGCGGC AGCGGGCCGG CTGGGACAGC TATGAAATCC

ACGTGGACGA CAGCCGGGAG TGTGTGGGGG GCCCCCAAAT CGCCCCCATC GTGGGCGGCA

CCGTGTCGGG AGTCGTGCTC ATCGGCATCC TCCTGCTGGC CATCTGGAAG GCTCTGACCC

ACCTGAGTGA CCTCCGCGAG TTCAAGCGAT TCGAGAAGGA GAAGCTCAGG TCCCAGTGGA

ACAACGACAA CCCCCTTTTC AAGAGCGCCA CCACCACAGT CATGAACCCC AGGTTTGCTG

AGAGTTAG
```

In a preferred embodiment, the Cys36Ser missense mutation is caused by a G→C transversion at nucleotide 107. This type of missense mutation at a single nucleotide in the gene sequence is referred to as a disease-causing single-nucleotide polymorphism.

The present invention also provides fragments of the nucleic acid molecules. Fragments of the nucleic acid molecules can be used to hybridize to target nucleic acid molecules to detect the presence of a mutation. The fragments must be long enough to be useful as a primer in a polymerase chain reaction (PCR) process or a probe in a ligase chain reaction (LCR) procedure. Preferred fragments are at least twelve bases in length.

The nucleic acid molecules or fragments need not be identical to the sequence of SEQ. ID. No. 10, excluding the polymorphism. Rather the nucleic acid molecule needs to have the polymorphism and sufficient identity to the remainder of SEQ. ID. No. 10 so that the nucleic acid molecule or fragment may be used to differentiate between genetic material having the mutation and genetic material lacking the mutation.

Suitable nucleic acid molecules may be identified by hybridization to the nucleic acid sequence of the gene encoding the leukocyte integrin β-2 subunit, preferably SEQ. ID. No. 10, with a Cys36Ser missense mutation in the gene, but not hybridization to SEQ. ID. No. 10. In a preferred embodiment, a suitable nucleic acid molecule hybridizes to the nucleic acid sequence of the gene encoding the leukocyte integrin β-2 subunit of SEQ. ID. No. 10 with a Cys36Ser missense mutation in the gene, but does not hybridize to SEQ. ID. No. 10, under stringent conditions. For example, sequences can be isolated that hybridize to a DNA molecule comprising a nucleotide sequence of 50 continuous bases of SEQ. ID. No. 10 including the Cys36Ser missense mutation under stringent conditions characterized by a hybridization buffer comprising 0.9M sodium citrate ("SSC") buffer at a temperature of 37° C. and remaining bound when subject to washing with the SSC buffer at 37° C.; and preferably in a hybridization buffer comprising 20% formamide in 0.9M saline/0.09M SSC buffer at a temperature of 42° C. and remaining bound when subject to washing at 42° C. with 0.2×SSC buffer at 42° C.

The nucleic acid molecules of the present invention may be linked to other nucleic acid molecules such as vectors or tags to facilitate amplification, purification, or identification.

The present invention also relates to a method for identifying dogs, particularly Irish Setters, which are carriers for or are affected with canine leukocyte adhesion deficiency. This method includes obtaining a biological sample from a dog and testing the biological sample for a Cys36Ser missense mutation in a gene encoding leukocyte integrin β-2 subunit, wherein the missense mutation in one allele is indicative of a carrier of canine leukocyte adhesion deficiency and the missense mutation in both alleles is indicative of a dog affected with canine leukocyte adhesion deficiency.

In a preferred embodiment, the biological sample is any tissue containing genomic DNA. Most preferably, the biological sample is blood, hair, cheek scrapings, semen, tissue biopsy, or saliva. In a most preferred embodiment, the biological sample is blood.

Methods of screening a biological sample for mutated nucleic acids can be carried out using either deoxyribonucleic acids ("DNA") or messenger ribonucleic acids ("mRNA") isolated from the biological sample. During periods when the gene is expressed, mRNA may be abundant and more readily detected. However, these genes are temporally controlled and, at most stages of development, the preferred material for screening is DNA.

In one embodiment of the invention, the testing of the genetic material in the biological sample is carried out by Oligonucleotide Ligation Assay ("OLA") (Landegren et el., "A Ligase-Mediated Gene Detection Technique," *Science*, 241:1077–1080 (1988); Landegren et al., "DNA Diagnostics—Molecular Techniques and Automation," *Science*, 242:229–237 (1988); U.S. Pat. No. 4,988,617 to Landegren et al., which are hereby incorporated by reference), as described below. The OLA protocol uses two oligonucleotides which are designed to be capable of hybridizing to abutting sequences of a single strand of a target. One of the oligonucleotides is biotinylated and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. OLA is capable of detecting point mutations. However, numerous methods for characterizing or detecting single nucleotide polymorphisms are known in the art and any of those methods are also suitable for the present invention.

One method of characterizing a polymorphism entails direct DNA. sequencing of the genetic locus that flanks and includes the polymorphism. Such analysis can be accomplished using either the "dideoxy-mediated chain termination method," also known as the "Sanger Method" (Sanger et al., "DNA Sequencing with Chain-Terminating Inhibitors."*Proc. Natl. Acad. Sci. USA*, 74:5463–5467 (1977), which is hereby incorporated by reference) or the "chemical degradation method," also known as the "Maxam-Gilbert method" (Maxam et al., "A New Method for Sequencing DNA," *Proc. Natl. Acad. Sci. USA*, 74:560–564 (1977), which is hereby incorporated by reference).

One example of a procedure for sequencing DNA molecules using arrays of oligonucleotides is disclosed in U.S. Pat. No. 5,202,231 to Drmanac et al., which is hereby incorporated by reference. This involves application of target DNA to a solid support to which a plurality of oligonucleotides are attached. Sequences are read by hybridization of segments of the target DNA to the oligonucleotides and assembly of overlapping segments of hybridized oligonucleotides. The array utilizes all possible oligonucleotides of a certain length between 11 and 20 nucleotides, but there is little information about how this array is constructed. See also Chetverin et al., "Sequencing of Pools of Nucleic Acids on Oligonucleotide Arrays," *BioSystems* 30: 215–31 (1993); WO 92/16655 to Khrapko et al.; Kuznetsova et al., "DNA Sequencing by Hybridization with Oligonucleotides Immobilized in Gel. Chemical Ligation as a Method of Expanding the Prospects for the Method," *Mol. Biol*. 28(20): 290–99(1994); Livits et al., "Dissociation of Duplexes Formed by Hybridization of DNA with Gel-Immobilized Oligonucleotides," *J. Biomolec. Struct. & Dynam*. 11(4): 783–812 (1994), which are hereby incorporated by reference.

WO 89/10977 to Southern, which is hereby incorporated by reference, discloses the use of a support carrying an array of oligonucleotides capable of undergoing a hybridization reaction for use in analyzing a nucleic acid sample for known point mutations genomic fingerprinting, linkage analysis, and sequence determination. The matrix is formed by laying nucleotide bases in a selected pattern on the support. This reference indicates that a hydroxyl linker group can be applied to the support with the oligonucleotides being assembled by a pen plotter or by masking.

Recently, single strand polymorphism assay ("SSPA") analysis and the closely related heteroduplex analysis methods have come into use as effectiy methods for screening for single-base polymorphisms (Orita et al., "Detection of Polymorphisms of Human DNA by Gel Electrophoresis as Single-Strand Conformation Polymorphisms," *Proc. Natl. Acad. Sci. USA*, 86:2766–2770 (1989), which is hereby incorporated by reference). In these methods, the mobility of PCR-amplified test DNA from clinical specimens is compared with the mobility of DNA amplified from normal sources by direct electrophoresis of samples in adjacent lanes of native polyacrylamide or o,her types of matrix gels. Single-base changes often alter the secondary structure of the molecule sufficiently to cause slight mobility differences between the normal and mutant ?CR products after prolonged electrophoresis.

Ligase chain reaction is another method of screening for mutated nucleic acids (see Barany, "Genetic Disease Detection and DNA Amplification Using Cloned Thermostable Ligase," *Proc. Nati. Acad. Sci. USA*, 88:189–193 (1991); Barany. "The Ligase Chain Reaction (LCR) in a PCR World," *PCR Methods and Applications*, 1:5–16 (1991); WO 90/17239 to Barany et al.; Barany et al., "Cloning, Overexpression and Nucleotide Sequence of a Thermostable DNA Ligase-Encoding Gene," *Gene*, 109:1–11 (1991); and Barany, "Genetic Disease Detection and DNA Amplification Using Cloned Thermostable Ligase," *Proc. Natl. Acad. Sci. USA*, 88:189–193 (1991), which are hereby incorporated by reference). In general, the LCR procedure is carried out with two pairs of oligonucleotide probes: one pair binds to one strand of the target sequence to be detected; the other pair binds to the other complementary strand of the target sequence to be detected. The reaction is carried out by, first, denaturing (e.g., separating) the strands of the target sequence, then reacting the separated strands with the two pairs of oligonucleotide probes in the presence of a heat stable ligase so that each pair of oligonucleotide probes hybridizes to target DNA and, if there is perfect complementarity at their junction, adjacent probes are ligated together. If such complementarity is lacking, no ligation occurs and the probes separate individually from the target sequence during denaturation. The ligated or unligated probes are then separated during the denaturation step. The process is cyclically repeated until the sequence has been amplified to the desired degree. Detection can then be carried out by electrophoresis or by capture hybridization on an array of DNA probes. Ligated and unligated probes can then be detected to identify the presence of a polymorphism.

The ligase detection reaction (LDR) process is another method for detecting a polymorphism. It is described generally in WO 90/17239 to Barany et al., Barany et al., "Cloning, Overexpression and Nucleotide Sequence of a Thermostable DNA Ligase-encoding, Gene," *Gene*, 109:1–11 (1991), and Barany, "Genetic Disease Detection and DNA Amplification Using Cloned Thermostable Ligase," *Proc. Natl. Acad. Sci. USA*, 88:189–193 (1991), the disclosures of which are hereby incorporated by reference. The ligase detection reaction is similar to the LCR technique; however, in LDR, there is only one pair of oligonucleotide probes which are complementary to one strand of the target sequence. While LCR provides an opportunity for exponential amplification, LDR achieves linear amplification.

Mundy et al. (U.S. Pat. No. 4,656.127, which is hereby incorporated by reference) discusses alternative methods for determining the identity of the nucleotide present at a particular polymorphic site. Mundy's methods employ a specialized exonuclease-resistant nucleotide derivative. A primer complementary to the allelic sequence immediately 3'-to the polymorphic site is permitted to hybridize to a target molecule obtained from a particular animal or human. If the polymorphic site on the target molecule contains a nucleotide that is complementary to the particular exonucleotide-resistant nucleotide derivative present, then that derivative will be incorporated by a polymerase onto the end of the hybridized primer. Such incorporation renders the primer resistant to exonuclease, and thereby permits its detection. Since the identity of the exonucleotide-resistant derivative of the sample is known, a finding that the primer has become resistant to exonucleases reveals that the nucleotide present in the polymorphic site of the target molecule was complementary to that of the nucleotide derivative used in the reaction. The Mundy method has the advantage that it does not require the determination of large amounts of extraneous sequence data. It has the disadvantages of destroying the amplified target sequences and unmodified primer and of being extremely sensitive to the rate of polymerase incorporation of the specific exonuclease-resistant nucleotide being used.

Recently, several primer-guided nucleotide incorporation procedures, i.e microsequencing methods, for assaying polymorphic sites in DNA have been described (Kornher et al., "Mutation Detection Using Nucleotide Analogs that Alter Electrophoretic Mobility," *Nucl. Acids. Res.*, 17:7779–7784 (1989); Sokolov, "Primer Extension Technique for the Detection of Single Nucleotide in Genomic DNA," *Nucl. Acids Res.*, 18:3671 (1990); Syvanen et al., "A Primer-Guided Nucleotide Incorporation Assay in the Genotyping of Apolipoprotein E," *Genomics*, 8:684–692 (1990); Kuppuswamy et al., "Single Nucleotide Primer Extension to Detect Genetic Diseases: Experimental Application to Hemophilia B (Factor IX) and Cystic Fibrosis Genes." *Proc. Nati. Acad. Sci. USA*, 88:1143–1147 (1991); Prezant et al., Trapped-Oligonucleotide Nucleotide Incorporation (TONI) Assay, a Simple Method for Screening Point Mutations." Hum. Mutat., 1:159–164 (1992); Ugozzoli et al., "Detection of Specific Alleles by Using Allele-specific Primer Extension Followed by Capture on Solid Support," *GATA*, 9:107–112 (1992); Nyren et al., "Solid Phase DNA Minisequencing by an Enzymatic Luminometric Inorganic Pyrophosphate Detection Assay," *Anal. Biochem.*, 208:171–175 (1993), which are hereby incorporated by reference). These methods differ from Genetic Bit TM Analysis ("GBA TM" discussed extensively below) in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen et al., "Identification of Individuals by Analysis of Biallelic DNA Markers, Using PCR and Solid-Phase Minisequencing," *Amer. J. Hum. Genet.*, 52:46–59 (1993), which is hereby incorporated by reference).

Cohen et al. (French Patent 2,650,840; PCT Application No. WO 91/02087, which are hereby incorporated by reference) discuss a solution-based method for determining the identity of the nucleotide of a polymorphic site. As in the Mundy method of U.S. Pat. No. 4,656,127, a primer is employed that is complementary to allelic sequences immediately 3'-to a polymorphic site. The method determines the identity of the nucleotide of that site using labeled dideoxynucleotide derivatives, which, if complementary to the nucleotide of the polymorphic site, will become incorporated onto the terminus of the primer.

An alternative method, known as Genetic Bit Analysis TM or GBA TM is described by Goelet et al. (PCT Application No. 92/15712, which is hereby incorporated by reference). In a preferred embodiment, the method of Goelet et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Application No. WO 91/02087, which are hereby incorporated by reference), the method of Goelet et al, is preferably a heterogeneous phase assay, in which the primer or the target molecule is immobilized to a solid phase. It is thus easier to perform, and more accurate than the method discussed by Cohen.

Other recently developed variations for detecting the presence of polymorphisms include: differential restriction endonuclease digestion (DRED), allele-specific oligonucleotide probing (ASOP), and ligase-mediated gene detection (LMGD). Additional methods of analysis would also be useful in this context, such as fluorescence resonance energy transfer (FRET) as disclosed by Wolf et al., "Detection of Nucleic Acid Hybridization by Nonradiative Fluorescence Resonance Energy Transfer," *Proc. Nat. Acad. Sci. USA*, 85: 8790–94 (1988), which is hereby incorporated by reference.

DRED analysis is accomplished in the following manner. If conditions occur including (1) a particular amplified cDNA segment contains a sequence variation that distinguishes an allele of a polymorphism and (2) this sequence variation is recognized by a restriction endonuclease, then the cleavage by the enzyme of a particular polynucleotide segment can be used to determine the alloantigen phenotype. In accomplishing this determination, amplified cDNA derived from platelet or red blood cell mRNA is digested and the resulting fragments are analyzed by size. The presence or absence of nucleotide fragments, corresponding to the endonuclease-cleaved fragments, determines which phenotype is present.

In ASOP analysis according to conventional methods, oligonucleotide probes are synthesized that will hybridize, under appropriate annealing conditions, exclusively to a particular amplified cDNA segment that contains a nucleotide sequence that distinguishes one allele from other alleles of a red blood cell or platelet membrane glycoprotein. This specific probe is discernibly labeled so that when it hybridizes to the allele distinguishing cDNA segment, it can be detected, and the specific allele is thus identified.

In the course of the third method of analysis, LMGD, as disclosed by Landegren et al., "A Ligase-Mediated Gene Detection Technique," *Science*, 241: 1077–80 (1988), which is hereby incorporated by reference, a pair of oligonucleotide probes are synthesized that will hybridize adjacently to each other, i.e., to a cDNA segment under appropriate annealing conditions, at the specific nucleotide that distinguishes one allele from other alleles of a red blood cell or platelet membrane glycoprotein. Each of the pair of specific probes is labeled in a different manner, and when it hybridizes to the allele-distinguishing cDNA segment, both probes can be ligated together by the addition of a ligase. When the ligated probes are isolated from the cDNA segments, both types of labeling can be observed together, confirming the presence of the allele-specific nucleotide sequence. Where the above-described pair of differently labeled probes bind to a nucleotide sequence containing a distinguishing nucleotide of a different allele, the probe pair is not ligatable and, after the probes are isolated from the cDNA segments. both types of labeling are observed separately.

WO 94/11530 to Cantor, which is hereby incorporated by reference, relates to the use of an oligonucleotide array to carry out a process of sequencing by hybridization. The oligonucleotides are duplexes having overhanging ends to which target nucleic acids bind and are then ligated to the non-overhanging portion of the duplex. The array is constructed by using streptavidin-coated filter paper which captures biotinylated oligonucleotides assembled before attachment.

WO 93/17126 to Chetverin, which is hereby incorporated by reference, uses sectioned, binary oligonucleotide arrays to sort and survey nucleic acids. These arrays have a constant nucleotide sequence attached to an adjacent variable nucleotide sequence, both bound to a solid support by a covalent linking moiety. The constant nucleotide sequence has a priming region to permit amplification by PCR of hybridized strands. Sorting is then carried out by hybridization to the variable region. Sequencing, isolating, sorting, and manipulating fragmented nucleic acids on these binary arrays are also disclosed. In one embodiment with enhanced sensitivity, the immobilized oligonucleotide has a shorter complementary region hybridized to it, leaving part of the oligonucleotide uncovered. The array is then subjected to hybridization conditions so that a complementary nucleic acid anneals to the immobilized oligonucleotide. DNA ligase is then used to join the shorter complementary region and the complementary nucleic acid on the array.

WO 92/10588 to Fodor et al., which is hereby incorporated by reference. discloses a process for sequencing, fingerprinting, and mapping nucleic acids by hybridization to an array of oligonucleotides. The array of oligonucleotides is prepared by a very large scale immobilized polymer synthesis which permits the synthesis of large, different oligonucleotides. In this procedure, the substrate surface is functionalized and provided with a linker group by which oligonucleotides are assembled on the substrate. The regions where oligonucleotides are attached have protective groups (on the substrate or individual nucleotide subunits) which are selectively activated. Generally, this involves imaging the array with light using a mask of varying configuration so that areas exposed are deprotected. Areas which have been deprotected undergo a chemical reaction with a protected nucleotide to extend the oligonucleotide sequence where imaged. A binary masking strategy can be used to build two or more arrays at a given time. Detection involves positional localization of the region where hybridization has taken place. See also U.S. Pat. Nos. 5,324,633 and 5,424,186 to Fodor et al., U.S. Pat. Nos. 5,143,854 and 5,405,783 to Pirrung et al., WO 90/15070 to Pirrung et al., Pease et al., "Light-generated Oligonucleotide Arrays for Rapid DNA Sequence Analysis", *Proc. Natl. Acad. Sci USA* 91: 5022–26 (1994), which are hereby incorporated by reference. Beattie et al., "Advances in Genosensor Research," *Clin. Chem.* 41(5): 700–09 (1995), which is hereby incorporated by reference, discloses attachment of previously assembled oligonucleotide probes to a solid support.

Landegren et al., "Reading Bits of Genetic Information: Methods for Single-Nucleotide Polymorphism Analysis," *Genome Research*, 8:769–776 (1998), which is hereby incorporated by reference, discloses a review of methods for single-nucleotide polymorphism analysis which are suitable for the present invention.

In another embodiment, testing the biological sample includes amplifying a region of the gene encoding a leukocyte integrin β-2 subunit to provide an amplified fragment before detecting any Cys36Ser missense mutation present in the biological sample.

Amplification of a selected, or target, nucleic acid sequence may be carried out by any suitable means, either to facilitate sequencing or for direct detection of polymorphisms. (See generally Kwoh et al., "Target Amplification Systems in Nucleic Acid-Based Diagnostic Approaches," *Am. Biotechnol. Lab.*, 8:14–25 (1990) which is hereby incorporated by reference.) Examples of suitable amplification techniques include, but are not limited to, polymerase chain reaction, ligase chain reaction ("LCR") strand displacement amplification (see generally, Walker et al., "Strand Displacement Amplification—An Isothermal, In Vitro DNA Amplification Technique," *Nucleic Acids Res.*, 20:1691–1696 (1992); Walker et al., "Isothermal In-Vitro Amplification of DNA By a Restriction Enzyme-DNA Polymerase System," *Proc. Natl. Acad. Sci. USA* 89:392–396 (1992), which are hereby incorporated by reference), transcription-based amplification (see Kwoh et al., "Transcription-Based Amplification System and Detection of Amplified Human Immunodeficiency Virus Type 1 With a Bead-Based Sandwich Hybridization Format," *Proc. Natl. Acad. Sci. USA* 86:1173–1177 (1989), which is hereby incorporated by reference), self-sustained sequence replication (or "3SR") (see Guatelli et al., "Isothermal In-Vitro Amplification of Nucleic Acids By a Multienzyme Reaction Modeled After Retroviral Replication," *Proc. Natl. Acad. Sci. USA* 87:1874–1878 (1990), which is hereby incorporated by reference), the Qβ replicase system (see Lizardi et al., "Exponential Amplification of Recombinant RNA Hybridization Probes," *Biotechnology*, 6:1197–1202 (1988), which is hereby incorporated by reference), nucleic acid sequence-based amplification (or "NASBA") (see Lewis, "Review of Progress in Developing Amplification Technologies Which May Compete With Roche Diagnostic Systems' Polymerase Chain Reaction (PCR)," *Genetic Engineering News*, 12(9):1, 8–9 (1992), which is hereby incorporated by reference), the repair chain reaction (or "RCR") (see Lewis, "Review of Progress in Developing Amplification Technologies Which May Compete With Roche Diagnostic Systems' Polymerase Chain Reaction (PCR).," *Genetic Engineering News*, 12(9):1, 8–9 (1992), which is hereby incorporated by reference), and boomerang DNA amplification (or "BDA") (see Lewis, "Review of Progress in Developing Amplification Technologies Which May Compete With Roche Diagnostic Systems' Polymerase Chain Reaction (PCR)," *Genetic Engineering News*, 12(9)):1, 8–9 (1992), which is hereby incorporated by reference). Polymerase chain reaction is currently preferred. Genomic sequence-specific amplification technologies, such a, the polymerase chain reaction (Mullis et al., "Specific Enzymatic Amplification of DNA in-Vitro the Polymerase Chain Reaction," *Cold Spring Harbor Symp. Quant. Biol.* 51:263–274 (1986); European Patent Application No. 50,424 to Erlich et al.; European Patent Application No. 84,796 to Erlich et al.; European Patent Application 258,017 to Erlich et al.; European Patent Application No. 237,362 to Erlich et al.; European Patent Application No. 201,184 to Mullis; U.S. Pat. No. 4,683,202 to Mullis et al.; U.S. Patent No. 4,582,788 to Erlich; Saiki et al., "Enzymatic Amplification of Beta Globin Genomic Sequences and Restriction Site Analysis for Diagnosis of Sickle Cell Anemia." *Science* 230: 1350–11354 (1985); and U.S. Patent No. 4,683,194 to Saiki et al., which are hereby incorporated by reference), may be employed to facilitate the recovery of the desired polynucleotides. In this method, primers complementary to opposite end portions of the selected sequence(s) are used to promote, in conjunction with thermal cycling, successive rounds of primer-initiated replication. The amplified sequence may be readily identified by a variety of techniques. This approach is particularly useful for detecting the presence of low-copy sequences in a polynucleotide-containing sample, e.g., for detecting pathogen sequences in a body-fluid sample.

One method that can be used to detect a single-nucleotide polymorphism is polymerase chain reaction restriction fragment length polymorphism (PCR-RFLP). In a preferred embodiment, this method includes amplification of leukocyte integrin β-2 subunit exon 3, using polymerase chain reaction (PCR), from the animal in question. Presence or absence of the G→C transversion at nucleotide 107 is then detected via utilization of the fact that it occurs within the recognition sequence for the restriction enzyme HinfI (recognition sequence GANTC). Where the G→C transversion at nucleotide 107 is present, the HinfI recognition sequence is correct (GACTC) and enzymatic cleavage proceeds. Where the G→C transversion at nucleotide 107 is absent, the HinfI recognition sequence is destroyed (GACTG) and enzymatic cleavage is prohibited. Following incubation with HinfI, the resulting PCR fragments are electrophoresed and their length indicates if cleavage has occurred and, therefore, the genotype at nucleotide 107.

Nickerson et al. have described a nucleic acid detection assay that combines attributes of PCR and OLA (Nickerson et al., "Automated DNA Diagnostics Using an Elisa-Based Oligonucleotide Ligation Assay," *Proc. Natl. Acad. Sci. USA*, 87:8923–8927 (1990), which is hereby incorporated by reference). In this method, PCR is used to achieve the exponential amplification of target DNA, which is then detected using OLA.

EXAMPLES

Example 1

Clinical Characterization of Affected Animals

Analysis of the expression of adhesion receptors CD11b and CD18 was performed as previously described (Trowald-Wigh et al., "Canine Neutrophil Adhesion Proteins and Fc-receptors in Healthy Dogs and Dogs with Adhesion Protein Deficiency, as Studied by Flow Cytometry," *Veterinary Immunology and Immunopathology*, 38:297–30 310 (1993), which is hereby incorporated by reference), with the exception that cells were prepared by lysis of red cells instead of dextran sedimentation. One part blood was mixed with nine parts Orthomune lysing solution (Ortho Diagnostic Systems, Raritan, N.J. USA), and lysing proceeded for 10 minutes. The cells were then washed twice with PBS, and resuspended in PBS with 5% FBS added. Leukocytes were immunostained with FITC-conjugated mouse anti-human CD11b (Clone BEAR1, Immunotech, Marseille, France) and FITC-conjugated mouse anti-human CD18 (Clone MHM23, Dako A/S, Glostrup. Denmark) antibodies. An irrelevant mouse monoclonal antibody (X927. Dako A/S) served as negative control. The samples were analyzed with a FACStarPLUS flow cytometer (Becton Dickinson Immunocytometry Systems, San José, Calif., USA).

The study included 15 affected Irish Setters from 9 different litters. Of these, 11 were clinically assessed at the Small Animal Clinic at the Swedish University of Agricultural Sciences in Uppsala (S1–11) and four animals, which were from England (UK1–4), were clinically assessed at Queen Mother Hospital, the Royal Veterinary College. University of London. The Swedish dogs were between 8 to 15 weeks of age and came from five different litters (Trowald-Wigh et al., "Leucocyte Adhesion Protein Deficiency in Irish Setter Dogs," *Veterinary Immunology and Immunopatholcgy*, 32:261–380 (1992), which is hereby incorporated by reference). All Swedish CLAD (dogs were euthanized before 7 months of age because of the severity of their symptoms. Among the four affected dogs from England two were siblings (UK2 and 3). UK1 and UK2 were euthanized before the age of one year while UK3 was euthanized at 14 months. Six healthy parents, four dams and two sires, and five healthy littermates were also included in the study. In addition, a population sample of 208 healthy Irish Setters from the UK was also DNA typed. DNA samples from other breeds included Labrador (5), American cocker spaniel (5), rottweiler (5), Siberian husky (5), poodle (5), border collie (4), German shepherd (1), Saluki (2), Swedish hunting dog 'Jämthund' (5), 'drever' (5), 'texvuren' (5) and Dachshund (1).

The 11 affected Swedish dogs were diagnosed as CLAD with granulocyte function tests. In addition, the leukocytes from five of these dogs were analyzed by flow-cytometry (Trowald-Wigh et al., "Leucocyte Adhesion Protein Deficiency in Irish Setter Dogs," *Veterinary Immunology and Immunopathology*, 32:261–380 (1992), which is hereby incorporated by reference). Two dams, one sire, and three littermates from Sweden showed normal expression of CD11b and CD 18 (Trowald-Wigh et al., "Canine Neutrophil Adhesion Proteins and Fc-receptors in Healthy Dogs and Dogs with Adhesion Protein Deficiency, as Studied by Flow Cytometry," *Veterinary Immunology and Immunopathology*, 38:297–310 (1993), which is hereby incorporated by reference). Two of the affected English dogs (UK1 and 2) had no expression of CD11b/CD18 whereas the other two (UK3 and 4) had partial expression, 5–10% of normal (FIGS. 1A–C). It should be noted that UK2 showing, no expression and UK3 showing partial expression were full-sibs. Two dams, one sire, and two littermates from England showed normal expression of CD11b/CD18.

Example 2

RT-PCR Analysis of ITGB2

Leukocytes were isolated as previously described (Trowald-Wigh et al., "Leucocyte Adhesion Protein Deficiency in Irish Setter Dogs," *Veterinary Imniunology and Immunopathogy*, 32:261–380 (1992), which is hereby incorporated by reference) and used to obtain mRNA using the Message Maker kit (Gibco BRL, Rockville, Md.). 200 ng of poly(A)+ mRNA was reverse transcribed with random primers (First-Strand cDNA Synthesis kit, Pharmacia Biotech, Uppsala, Sweden) before four overlapping sets of gene specific primers were used to amplify ITGB2 DNA for sequence analysis: CD7 (5'GGACATGCTGNGCCNGYGCYC-3') (SEQ. ID. No. 11) and LA87 (5'-GAGGTCRTCMASCATGGAGTAGG-3') (SEQ. ID. No. 12) (exons two to five); SG 1 (5'-GTTCGCTGTGACACCCGAGAG-3') (SEQ. ID. No. 13) and LA86 (5'-TGACCTTTACCTGGAAGGTGA-3') (SEQ. ID. No. 14) (exons four to 11); SG3 (5'-AGCACCCTCAAGGTCACCTATGACTC-3') (SEQ. ID. No. 15) and SG2 (5'-CTTCTCGAATCGCTTGAACTCGC-3') (SEQ. ID. No. 16) (exons 10 to 15); CD18 (5'-TGTCGGGAGTCGTGCTCATCGG-3') (SEQ. ID. No. 17) and CD19 (5'-GTCCCTGGAGGAGCCTGACGG-3') (SEQ. ID. No. 18) (exon 15 to the 3 UTR). Amplification of 30 ng of cDNA was performed in 10 μl reactions each containing 0.2 mM dNTPs. 1.5 mM MgCl$_2$, 1.0 pmol of both forward and reverse primer, 5% DMSO and AmpliTaq Gold DNA polymerase and reaction buffer (Perkin-Elmer, Fester City, Calif.). The cycling conditions included an initial incubation at 95° C. for 10 minutes followed by 32 cycles at 94° C. (45 sec), 55° C. (45 see), and 72° C. (45 sec) before resulting products were gel purified and cloned using the Sureclone ligation kit (Pharmacia Biotech, Uppsala, Sweden). At least two plasmid clones per fragment from both a normal and CLAD animal were sequenced using either the vector or gene specific primers.

Leukocytes were isolated and MRNA was extracted from a blood sample from a healthy Irish Setter with no familial history of CLAD. The mRNA was reversed transcribed into cDNA and a set of primer combinations were used to amplify and sequence the entire ITGB2 coding sequence of 2,067 bp except 7 bp in the 5' end that were included in the primer sequence. Translation showed high amino acid secuence identity with the homologous sequences of cattle and pig (both 81.3%). human (80.9%) and mouse (79.5%). In addition, the highly conserved region consisting of residues 102–344 (Huang et al., "Folding of the Conserved Domain But Not of Flanking Regions in the Integrin β2 Subunit Requires Association With the α Subunit," *Proc. Natl. Acad. Sci. USA*, 94:3156–3161 (1997), which is hereby incorporated by reference) was also highly conserved in the canine molecule showing between 93–96% sequence identity to the species above (FIGS. 2A and B).

Figures 3A, 3B:
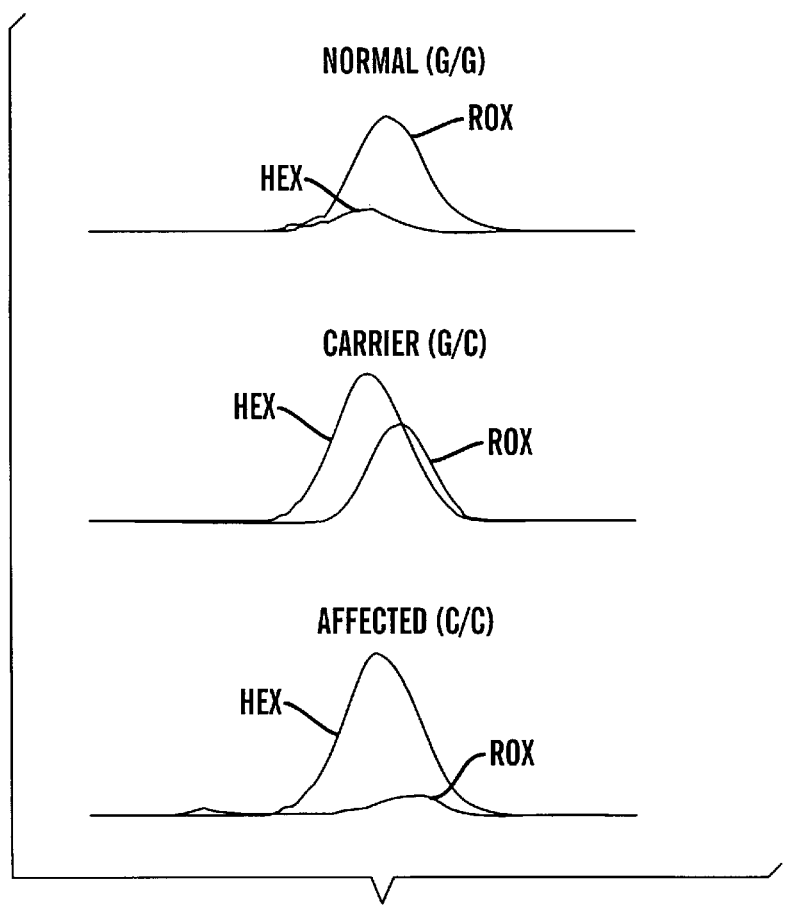
FIGS. 3A and 3B show the detection of a missense mutation associated with CLAD.

RT-PCR analysis was carried out using a blood sample from one animal diagnosed with CLAD. The CDNA sequences from the normal and the affected dog were identical in length and sequence except for a single nucleotide substitution, a G to C transversion at position 107 (FIG. 3A). This point mutation led to a replacement of cysteine by serine (C36S) in the affected animal. This cysteine was conserved in the ITGB2 molecule across species (FIG. 2).

Example 3

Mutation Detection

Amplification of ITGB2 exon 3 from genomic DNA was performed in 20 µl reactions as above using primer CD13 (5'-CGTCCTGCCAGGAGTCCACCAAGTA-3') (SEQ. ID. No. 19) and CD14 (5'-GCTTCTGGCACCAGGCGCAGCCG-3') (SEQ. ID. No. 20). The PCR product (2 µl) was used for allele discrimination at nicleotide position 107 using the oligonucleotide ligation assay (OLA) in the ligase detection reaction (LDR) process (Landegren et al., "A Ligase-mediated Gene Detection Technique." *Science* 241, 1077–80 (1988), which is hereby incorporated by reference). The OLA method was carried out as a gel-based assay rather than the standard solid-phase procedure. Each 10 µl OLA reaction contained 2.0 pmol of each probe OLA–C (5'-HEX-CACGTGCCGGGACTC-5') (SEQ. ID. No. 21), OLA-G (5'-ROX-GCACGTGCCGGGACTG-3') (SEQ. ID. No. 22), and OLA-common (5'-phosphate-TGTGGAGTCGGGGCC-3') (SEQ. ID. No. 23), 1.5 U of thermostable ligase Ampligase, and reaction buffer (Epicentre Technologies, Madison, Wis.) and 5 µl of CD13/ CD14 PCR product. The following thermocycling profile was repeated 25 times: denaturation at 94° C. for 30 seconds, probe annealing at 55° C. for 30 seconds, and ligation at 45° C. for 60 seconds. After OLA cycling, 0.5 µl of product was heat denatured at 94° C. for 2 minutes, cooled on ice, and loaded onto a 4% acrylamide denaturing gel for electrophoresis on an ABI377 DNA sequencer (Perkin Elmer, Foster City, Calif.). The resulting fragment lengths and peak fluorescence were analyzed using the GeneScan software (Perkin Elmer, Foster City, Calif.).

An OLA based test was developed as a screening method for the C36S mutation. This method was used to determine the genotype of DNA samples collected from 11 animals originating from six separate Swedish Irish Setter pedigrees involving CLAD cases. FIG. 3B shows example OLA output and Table 1, below, shows that all affected animals were homozvgous for the C36S mutation, while each parent was heterozygous for the mutation.

TABLE 1

Association between the CLAD and Phenotype and the ITGB2 C36S Mutation Assessed by an OLA Analysis

| Animals | Number Tested | Genotype G/G | G/C | C/C |
|---|---|---|---|---|
| CLAD Pedigree Animals | | | | |
| Affected dogs | 12 | 0 | 0 | 12 |
| Parents to affected dogs | 6 | 0 | 6 | 0 |
| Litter mates to affected dogs | 5 | 3 | 2 | 0 |
| Unrelated Healthy Animals | | | | |
| Irish Setter | 208 | 189 | 19 | 0 |
| Other breeds[1] | 48 | 48 | 0 | 0 |

[1]See Example 1 for description of other breeds

In addition, typing of healthy littermates to affected animals showed these to be either heterozygous or homozygous normal. The results were consistent with the autosomal recessive inheritance of the disease.

To further investigate the association of C36S to CLAD, a total of 208 healthy animals from the UK Irish Setter population were screened. None of the healthy animals were homozygous for the C36S mutation; however a total of 19 animals were heterozygous (Table 1). To date, no cases of CLAD have been reported in dog breeds other than Irish Setter. DNA samples from 48 animals representing 12 other breeds were screened and all were found to be homozygous normal C36 (Table 1). However, the same mutation or another mutation in this gene in other dog breeds could be detected by the same technology described herein.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated nucleic acid molecule encoding canine leukocyte integrin β-2 subunit having a Cys36Ser missense mutation in the nucleic acid sequence according to SEQ. ID. No. 10, wherein said missense mutation is indicative of a carrier of canine leukocyte adhesion deficiency and said missense mutation is caused by a G→C transversion at nucleotide 107 in the nucleic acid of SEQ. ID. No. 10.

2. An isolated nucleic acid molecule comprising:
  a DNA molecule having the nucleotide sequence selected from the group consisting of SEQ. ID. No. 11, SEQ. ID. No. 12, SEQ. ID. No. 13, SEQ. ID. No. 14, SEQ. ID. No. 15, SEQ. ID. No. 16, SEQ. ID. No. 17, SEQ. ID. No. 18, SEQ. ID. No. 19, SEQ. ID. No. 20, SEQ. ID. No. 21, SEQ. ID. No. 22, and SEQ. ID. No. 23.

3. A method for identifying Irish Setter dogs which are carriers of or are affected with canine leukocyte adhesion deficiency, said method comprising:
  obtaining a biological sample from an Irish Setter dog and testing the biological sample for a Cys36Ser missense mutation in a gene encoding leukocyte integrin β-2 subunit, wherein the Cvs36Ser missense mutation is caused by a G→C transversion at nucleotide 107 in the nucleic acid of SEQ. ID. No. 10 and the missense mutation in one allele is indicative of a carrier of canine leukocyte adhesion deficiency and the missense mutation in both alleles is indicative of an Irish Setter dog affected with canine leukocyte adhesion deficiency.

4. The method according to claim 3, wherein said testing is carried out by an oligonlicleotide ligation assay.

5. The method according to claim 3, wherein said testing is carried out by direct sequence analysis.

6. The method according to claim 3, wherein said detecting is carried out by subjecting the biological sample to conditions effective to hybridize DNA molecules with the missense mutation to a probe specific for the sequence of the missense mutation.

7. The method according to claim 3, wherein said detecting is carried out by digesting the biological sample with a restriction endonuclease.

8. The method according to claim 3, wherein said testing is carried out by ligase detection reaction.

9. The method according to claim 3, wherein said testing is carried out by single strand polymorphism assay.

10. The method according to claim 3, wherein said testing is carried out by ligase chain reaction.

11. The method according to claim 3, wherein said testing is carried out by PCR-based restriction fragment length polymorphism.

12. The method according to claim 3, wherein said testing comprises:

amplifying a region of the gene encoding a leukocyte integrin β-2 subunit to provide an amplified fragment before detecting any Cvs36Ser missense mutation present in the biological sample.

13. The method according to claim 3, wherein the nucleic acid is a deoxyribonucleic acid.

14. The method according to claim 3, Wherein the nucleic acid is a messenger ribonucleic acid.

15. The method according to claim 3, wherein the biological sample is any tissue containing genomic DNA.

16. The method according to claim 15, wherein the biological sample is blood, hair, check scrapings, semen, tissue biopsy, or saliva.

* * * * *

SEQUENCE LISTING

<160> NUMBER OF SEQ ID NOS: 23

<210> SEQ ID NO 1
<211> LENGTH: 344
<212> TYPE: PRT
<213> ORGANISM: Canis familiaris

<400> SEQUENCE: 1

```
Met Leu Arg His Ser Ser Leu Leu Thr Leu Glu Gly Leu Leu Phe
 1               5                  10                  15

Leu Trp Ala Ala Ser Cys Gln Glu Cys Thr Lys Tyr Lys Val Ser Thr
             20                  25                  30

Cys Arg Asp Cys Val Glu Ser Gly Pro Gly Cys Ala Trp Cys Gln Lys
         35                  40                  45

Leu Asn Phe Thr Gly Leu Gly Glu Pro Asp Ser Val Arg Cys Asp Thr
     50                  55                  60

Arg Glu Gln Leu Leu Lys Gly Cys Ala Ala Asp Ile Met Asp
65                  70                  75                  80

Pro Gln Ser Leu Ala Glu Ile Gln Glu Asp Lys Lys Gly Arg Gln
                 85                  90                  95

Gln Leu Ser Pro Gln Lys Val Thr Leu Tyr Leu Arg Pro Gly Gln Ala
             100                 105                 110

Ala Ala Phe Asn Val Thr Phe Arg Arg Ala Lys Gly Tyr Pro Ile Asp
             115                 120                 125

Leu Tyr Tyr Leu Met Asp Leu Ser Tyr Ser Met Leu Asp Asp Leu Ile
     130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                 165                 170                 175

Leu Pro Phe Val Asn Thr His Pro Glu Lys Leu Lys Asn Pro Cys Pro
             180                 185                 190

Asn Lys Glu Lys Glu Cys Gln Ala Pro Phe Ala Phe Arg His Val Leu
             195                 200                 205

Lys Leu Thr Asn Asn Ser Asn Lys Phe Gln Thr Glu Val Gly Lys Gln
     210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Gln Ile Gly Trp Arg Asn Val Thr
                 245                 250                 255

Arg Leu Leu Val Phe Ala Thr Asp Asp Gly Phe His Phe Ala Gly Asp
             260                 265                 270

Gly Lys Leu Gly Ala Ile Leu Thr Pro Asn Asp Gly Arg Cys His Leu
         275                 280                 285

Glu Asp Asn Met Tyr Lys Arg Ser Asn Glu Phe Asp Tyr Pro Ser Val
     290                 295                 300

Gly Gln Leu Ala His Lys Leu Ala Glu Ser Asn Ile Gln Pro Ile Phe
305                 310                 315                 320

Ala Val Thr Lys Arg Met Val Thr Tyr Glu Lys Leu Thr Glu Val
                 325                 330                 335

Ile Pro Lys Ser Ala Val Gly Glu
             340
```

```
<210> SEQ ID NO 2
<211> LENGTH: 344
<212> TYPE: PRT
<213> ORGANISM: Bos sp.

<400> SEQUENCE: 2

Met Leu Arg Gln Arg Pro Gln Leu Leu Leu Ala Gly Leu Leu Ala
 1               5                  10                  15

Leu Gln Ser Val Leu Ser Gln Glu Cys Thr Asn Tyr Lys Val Ser Thr
                 20                  25                  30

Cys Arg Asp Cys Ile Glu Ser Gly Pro Gly Cys Ala Trp Cys Gln Lys
             35                  40                  45

Leu Asn Phe Thr Gly Gln Gly Glu Pro Asp Ser Ile Arg Cys Asp Thr
         50                  55                  60

Arg Ala Glu Leu Leu Ser Lys Gly Cys Pro Ala Asp Asp Ile Met Glu
 65                  70                  75                  80

Pro Lys Ser Leu Ala Glu Thr Arg Asp Ser Gln Ala Gly Ser Arg Lys
                 85                  90                  95

Gln Leu Ser Pro Gln Glu Val Thr Leu Tyr Leu Arg Pro Gly Gln Ala
            100                 105                 110

Val Ala Phe Asn Val Thr Phe Arg Arg Ala Lys Gly Tyr Pro Ile Asp
            115                 120                 125

Leu Tyr Tyr Leu Met Asp Leu Ser Tyr Ser Met Val Asp Asp Leu Val
        130                 135                 140

Asn Val Lys Lys Leu Gly Gly Asp Leu Leu Arg Ala Leu Asn Gly Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Glu Cys Gln Pro Pro Phe Ala Phe Arg His Val Leu
            195                 200                 205

Lys Leu Thr Asp Asn Ser Lys Gln Phe Glu Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Ser Ser Asn Glu Phe Asp Tyr Pro Ser Val
    290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Glu Ile
                325                 330                 335

Ile Pro Lys Ser Ala Val Gly Glu
            340

<210> SEQ ID NO 3
<211> LENGTH: 344
<212> TYPE: PRT
<213> ORGANISM: Homo sapiens
```

<400> SEQUENCE: 3

```
Met Leu Gly Leu Arg Pro Pro Leu Ala Leu Val Gly Leu Leu Ser
 1               5                  10                  15

Leu Gly Cys Val Leu Ser Gln Glu Cys Thr Lys Phe Lys Val Ser Ser
                20                  25                  30

Cys Arg Glu Cys Ile Glu Ser Gly Pro Gly Cys Thr Trp Cys Gln Lys
            35                  40                  45

Leu Asn Phe Thr Gly Pro Gly Asp Pro Asp Ser Ile Arg Cys Asp Thr
        50                  55                  60

Arg Pro Gln Leu Leu Met Arg Gly Cys Ala Ala Asp Asp Ile Met Asp
 65                 70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
                100                 105                 110

Ala Ala Phe Asn Val Thr Phe Arg Arg Ala Lys Gly Tyr Pro Ile Asp
            115                 120                 125

Leu Tyr Tyr Leu Met Asp Leu Ser Tyr Ser Met Leu Asp Asp Leu Arg
        130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asn Asn Ser Asn Gln Phe Gln Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
    290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu
                340
```

<210> SEQ ID NO 4
<211> LENGTH: 344
<212> TYPE: PRT
<213> ORGANISM: Sus sp.

<400> SEQUENCE: 4

```
Met Leu Cys Arg Cys Ser Pro Leu Leu Leu Val Gly Leu Leu Thr
 1               5                  10                  15
```

```
Leu Arg Ser Ala Leu Ser Gln Glu Cys Ala Lys Tyr Lys Val Ser Thr
            20                  25                  30

Cys Arg Asp Cys Ile Glu Ser Gly Pro Gly Cys Ala Trp Cys Gln Lys
        35                  40                  45

Leu Asn Phe Ser Gly Gln Gly Glu Pro Asp Ser Val Arg Cys Asp Thr
    50                  55                  60

Arg Glu Gln Leu Leu Ala Lys Gly Cys Val Ala Asp Asp Ile Val Asp
65                  70                  75                  80

Pro Arg Ser Leu Ala Glu Thr Gln Glu Asp Gln Ala Gly Gly Gln Lys
                85                  90                  95

Gln Leu Ser Pro Gln Lys Val Thr Leu Tyr Leu Arg Pro Gly Gln Ala
            100                 105                 110

Ala Thr Phe Asn Val Thr Phe Arg Arg Ala Lys Gly Tyr Pro Ile Asp
            115                 120                 125

Leu Tyr Tyr Leu Met Asp Leu Ser Tyr Ser Met Leu Asp Asp Leu Ile
    130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Glu Lys Leu Arg Asn Pro Cys Pro
            180                 185                 190

Asn Lys Glu Lys Glu Cys Gln Ala Pro Phe Ala Phe Arg His Val Leu
        195                 200                 205

Lys Leu Thr Asp Asn Ser Asn Gln Phe Gln Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
            275                 280                 285

Glu Asp Asn Leu Tyr Lys Ser Ser Asn Glu Phe Asp Tyr Pro Ser Val
    290                 295                 300

Gly Gln Leu Ala His Lys Leu Ala Glu Ser Asn Ile Gln Pro Ile Phe
305                 310                 315                 320

Ala Val Thr Lys Lys Met Val Lys Thr Tyr Glu Lys Leu Thr Asp Ile
                325                 330                 335

Ile Pro Lys Ser Ala Val Gly Glu
            340

<210> SEQ ID NO 5
<211> LENGTH: 344
<212> TYPE: PRT
<213> ORGANISM: Mus sp.

<400> SEQUENCE: 5

Met Leu Gly Pro His Ser Leu Leu Ala Leu Ala Gly Leu Phe Phe
1               5                   10                  15

Leu Gly Ser Ala Val Ser Gln Glu Cys Thr Lys Tyr Lys Val Ser Ser
            20                  25                  30

Cys Arg Asp Cys Ile Gln Ser Gly Pro Gly Cys Ser Trp Cys Gln Lys
        35                  40                  45
```

```
Leu Asn Phe Thr Gly Pro Gly Glu Pro Asp Ser Leu Arg Cys Asp Thr
 50                  55                  60

Arg Ala Gln Leu Leu Lys Gly Cys Pro Ala Asp Asp Ile Met Asp
 65              70                  75                  80

Pro Arg Ser Ile Ala Asn Pro Glu Phe Asp Gln Arg Gly Gln Arg Lys
                 85                  90                  95

Gln Leu Ser Pro Gln Lys Val Thr Leu Tyr Leu Arg Pro Gly Gln Ala
             100                 105                 110

Ala Ala Phe Asn Val Thr Phe Arg Arg Ala Lys Gly Tyr Pro Ile Asp
             115                 120                 125

Leu Tyr Tyr Leu Met Asp Leu Ser Tyr Ser Met Leu Asp Asp Leu Asn
 130                 135                 140

Asn Val Lys Lys Leu Gly Gly Asp Leu Leu Gln Ala Leu Asn Glu Ile
145                 150                 155                 160

Thr Glu Ser Gly Arg Ile Gly Phe Gly Ser Phe Val Asp Lys Thr Val
                 165                 170                 175

Leu Pro Phe Val Asn Thr His Pro Glu Lys Leu Arg Asn Pro Cys Pro
                 180                 185                 190

Asn Lys Glu Lys Ala Cys Gln Pro Pro Phe Ala Phe Arg His Val Leu
             195                 200                 205

Lys Leu Thr Asp Asn Ser Asn Gln Phe Gln Thr Glu Val Gly Lys Gln
 210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                 245                 250                 255

Arg Leu Leu Val Phe Ala Thr Asp Asp Gly Phe His Phe Ala Gly Asp
                 260                 265                 270

Gly Lys Leu Gly Ala Ile Leu Thr Pro Asn Asp Gly Arg Cys His Leu
             275                 280                 285

Glu Asp Asn Met Tyr Lys Arg Ser Asn Glu Phe Asp Tyr Pro Ser Val
 290                 295                 300

Gly Gln Leu Ala His Lys Leu Ser Glu Ser Asn Ile Gln Pro Ile Phe
305                 310                 315                 320

Ala Val Thr Lys Lys Met Val Lys Thr Tyr Glu Lys Leu Thr Glu Ile
                 325                 330                 335

Ile Pro Lys Ser Ala Val Gly Glu
             340

<210> SEQ ID NO 6
<211> LENGTH: 27
<212> TYPE: DNA
<213> ORGANISM: Canis familiaris

<400> SEQUENCE: 6
agcacgtgcc gggactgtgt ggagtcg                                          27

<210> SEQ ID NO 7
<211> LENGTH: 27
<212> TYPE: DNA
<213> ORGANISM: Canis familiaris

<400> SEQUENCE: 7
agcacgtgcc gggactctgt ggagtcg                                          27
```

```
<210> SEQ ID NO 8
<211> LENGTH: 9
<212> TYPE: PRT
<213> ORGANISM: Canis familiaris

<400> SEQUENCE: 8

Ser Thr Cys Arg Asp Cys Val Glu Ser
  1               5

<210> SEQ ID NO 9
<211> LENGTH: 9
<212> TYPE: PRT
<213> ORGANISM: Canis familiaris

<400> SEQUENCE: 9

Ser Thr Cys Arg Asp Ser Val Glu Ser
  1               5

<210> SEQ ID NO 10
<211> LENGTH: 2348
<212> TYPE: DNA
<213> ORGANISM: Canis familiaris

<400> SEQUENCE: 10
gaattcccac cgaggtcacc ggcatcagcg gggacatgct cgcgccacagc tccctgctgc      60
tcaccctgga gggtctgctc tttctctggg ccgcgtcctg ccaggagtgc accaagtaca     120
aagtgagcac gtgccgggac tgtgtggagt cggggcccgg ctgcgcctgg tgccagaagc     180
tgaacttcac tgggctaggg gagcccgact ccgttcgctg tgacacccga gagcagctgc     240
tgctgaaagg atgtgcggct gacgacatca tggaccctca gagcctggcc gagatccagg     300
aggacaagaa gggcggccgg cagcagctgt ccccgcagaa agtgacgctc tacctgagac     360
caggtcaggc ggctgccttc aatgtgacct tccggcgggc caagggctac ccatcgacc      420
tgtactacct gatggatctg tcctactcca tgctggacga cctcatcaac gtcaagaagc     480
tgggggggcga cctgctgcgg gcgctcaacg aaatcaccga gtccggccgc atcggcttcg     540
ggtctttcgt ggacaagacg gtgctcccct tcgtcaacac gcaccccgag aagctgaaga     600
acccgtgccc caacaaggag aaggagtgcc aggcgccgtt cgccttcaga cacgtgctga     660
agctcacgaa caactccaac aagttccaga cggaggtcgg gaagcagctg atctcgggga     720
acctggacgc gcccgagggc gggctggatg ccatgatgca ggtcgccgcg tgcccggagc     780
aaaatcggctg gcgcaacgtc actcggctgc tggtgttcgc cacggacgac ggcttccact     840
ttgcgggcga cgggaagctg gtgccatcc tgacccccaa tgacggccgc tgccacctgg     900
aggacaacat gtacaagagg agcaatgaat ttgactaccc gtcggtgggc cagctggcac     960
acaaactggc cgaaagcaac atccagccca tcttcgcggt gaccaagaga atggtgacga    1020
cctatgagaa gctcaccgag gtcatcccca gtcagcggg cggggagctg tcggacgatt    1080
ccagcaacgt ggtccagctc atcaagaacg cctacaacaa actgtcctcc agggtcttcc    1140
tggaccacag cctggcccccc agcaccctca ggtcaccta tgactccttc tgcagtaacg    1200
gggtgtcgca ggtggaccag cccagagggg actgcgacgg cgtccagatc aacgtcccga    1260
tcaccttcca ggtgaaggtc acggccacgg agtgcatcca ggagcagtcg tttataatcc    1320
gggcactggg cttcacggac acagtgaccg tgcacgtcat ccccagtgc gagtgccagt    1380
gccgggacgt gggccaggac cacggcctct gcagcggcaa gggctccctg gagtgtggca    1440
tctgcaggtg tgaggctggc tacatcggga agaactgcga gtgcctgacg cacggccgca    1500
```

```
gcagccagga gctggagggc agctgtcgga gggacaacag ctctctcatc tgctcgggcc    1560
tgggggactg cctctgcggg cagtgcgtgt gccacaggag cgacgttccc aacaagaaca    1620
tcttcgggcg ctactgcgag tgtgacaatg tcaactgcga cgctatgac gggcaggtgt     1680 gcggggtaa agttcggggc tcctgcaact gcggcaagtg ccagtgtgag cagaactacg     1740
agggctcggc gtgccagtgc gtgaagtcca cccaggctg cctgagcacg gagggcatcg     1800
agtgcaacgg gcgcggccgc tgtcgctgta acgtgtgcga gtgcgacggg ggctaccagc    1860
cgccgctgtg cggggactgc ctgggctgcc cgtcgccctg tggccggtac atcacctgtg    1920
cccagtgcct gaagttcaag cagggcccct cggggaggaa ctgcagcgtg gagtgtggga    1980
acgtgggcct gctgagcaaa cccccagaga aggggcgcag gtgcaaggag cgggatctgg    2040
agggctgctg gatcacctac acgctgcggc agcgggccgg ctgggacagc tatgaaatcc    2100
acgtggacga cagccgggag tgtgtggggg gcccccaaat cgcccccatc gtgggcggca    2160
ccgtgtcggg agtcgtgctc atcggcatcc tcctgctggc catctggaag gctctgaccc    2220
acctgagtga cctccgcgag ttcaagcgat tcgagaagga gaagctcagg tcccagtgga    2280
acaacgacaa cccccttttc aagagcgcca ccaccacagt catgaacccc aggtttgctg    2340
agagttag                                                             2348

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:
      Primer CD7
<220> FEATURE:
<221> NAME/KEY: unsure
<222> LOCATION: (11)
<223> OTHER INFORMATION: N at position 11 is A, C, G, or T
<220> FEATURE:
<221> NAME/KEY: unsure
<222> LOCATION: (15)
<223> OTHER INFORMATION: N at position 15 is A, C, G, or T

<400> SEQUENCE: 11
ggacatgctg ngccngygcy c                                              21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:
      Primer LA87

<400> SEQUENCE: 12
gaggtcrtcm ascatggagt agg                                            23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
      Primer SG1

<400> SEQUENCE: 13
gttcgctgtg cacccgaga g                                               21

<210> SEQ ID NO 14
```

```
<211> LENGTH: 21
<212> TYPE: DNA
<213> ORGANISM: Artificial Sequence
<220> FEATURE:
<223> OTHER INFORMATION: Description of Artificial Sequence:
      Primer LA86

<400> SEQUENCE: 14
tgacctttac ctggaaggtg a                                                 21

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:
      Primer SG3

<400> SEQUENCE: 15
agcaccctca aggtcaccta tgactc                                            26

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
      Primer SG2

<400> SEQUENCE: 16
cttctcgaat cgcttgaact cgc                                               23

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:
      Primer CD18

<400> SEQUENCE: 17
tgtcgggagt cgtgctcatc gg                                                22

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:
      Primer CD19

<400> SEQUENCE: 18
gtccctggag gagcctgacg g                                                 21

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:
      Primer CD13

<400> SEQUENCE: 19
cgtcctgcca ggagtccacc aagta                                             25

<210> SEQ ID NO 20
<211> LENGTH: 23
```

```
<212> TYPE: DNA
<213> ORGANISM: Artificial Sequence
<220> FEATURE:
<223> OTHER INFORMATION: Description of Artificial Sequence:
      Primer CD14

<400> SEQUENCE: 20
gcttctggca ccaggcgcag ccg                                         23

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence:
      Probe OLA-C

<400> SEQUENCE: 21
cacgtgccgg gactc                                                  15

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence:
      Probe OLA-G

<400> SEQUENCE: 22
gcacgtgccg ggactg                                                 16

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence:
      Probe OLA-common

<400> SEQUENCE: 23
tgtggagtcg gggcc                                                  15
```